(12) United States Patent
Tagawa et al.

(10) Patent No.: US 8,933,247 B2
(45) Date of Patent: Jan. 13, 2015

(54) SUCCINIMIDE COMPOUND, LUBRICATING OIL ADDITIVE, AND LUBRICATING OIL COMPOSITION

(75) Inventors: Kazuo Tagawa, Tokyo (JP); Miho Endou, Tokyo (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 289 days.

(21) Appl. No.: 13/638,170

(22) PCT Filed: Mar. 29, 2011

(86) PCT No.: PCT/JP2011/057876
§ 371 (c)(1),
(2), (4) Date: Oct. 26, 2012

(87) PCT Pub. No.: WO2011/122637
PCT Pub. Date: Oct. 6, 2011

(65) Prior Publication Data
US 2013/0040865 A1  Feb. 14, 2013

(30) Foreign Application Priority Data

Mar. 30, 2010  (JP) ................................ P2010-078672
Apr. 5, 2010   (JP) ................................ P2010-087211

(51) Int. Cl.
  *C07D 403/06* (2006.01)
  *C10M 133/56* (2006.01)
  *C07D 207/412* (2006.01)

(52) U.S. Cl.
  CPC ........... *C07D 403/06* (2013.01); *C10M 133/56* (2013.01); *C07D 207/412* (2013.01); *C10M 2203/1006* (2013.01); *C10M 2215/28* (2013.01); *C10M 2223/00* (2013.01); *C10N 2220/021* (2013.01); *C10N 2230/06* (2013.01); *C10N 2240/042* (2013.01); *C10N 2240/045* (2013.01); *C10M 2209/084* (2013.01); *C10M 2215/064* (2013.01); *C10M 2219/04* (2013.01); *C10M 2219/044* (2013.01); *C10M 2219/046* (2013.01); *C10M 223/041* (2013.01)
  USPC ........... 548/468; 508/261; 508/266; 508/294; 508/291; 548/547

(58) Field of Classification Search
  USPC ........... 548/468, 547; 508/261, 266, 291, 294
  See application file for complete search history.

(56) References Cited

U.S. PATENT DOCUMENTS

| | | |
|---|---|---|
| 4,326,973 A | 4/1982 | Hammond et al. |
| 5,744,430 A | 4/1998 | Inoue et al. |
| 5,922,656 A | 7/1999 | Yoshimura et al. |
| 6,114,542 A | 9/2000 | Cherpeck |
| 6,352,566 B1 | 3/2002 | Cherpeck |
| 6,548,458 B2 * | 4/2003 | Loper ............................ 508/291 |
| 2005/0124506 A1 | 6/2005 | Shiga et al. |

FOREIGN PATENT DOCUMENTS

| | | |
|---|---|---|
| CA | 2 280 238 | 2/2001 |
| EP | 0982322 | 3/2000 |

(Continued)

OTHER PUBLICATIONS

Search Report for counterpart EP Patent Application No. 11762861. 0, mailed on Sep. 2, 2013.

(Continued)

*Primary Examiner* — James Goloboy
(74) *Attorney, Agent, or Firm* — Greenblum & Bernstein, P.L.C.

(57) ABSTRACT

The present invention provides a succinimide compound represented by the following formula (1-1) or (1-2), and a lubricating oil additive and a lubricating oil composition which contain the succinimide compound.

[Chemical Formula 1]

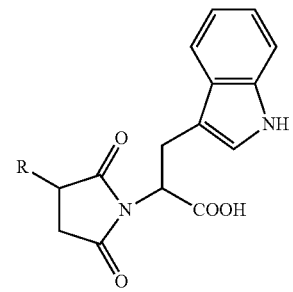

(1-1)

wherein R represents an alkyl group or an alkenyl group having a number-average molecular weight of 500 or greater and less than 5000.

[Chemical Formula 2]

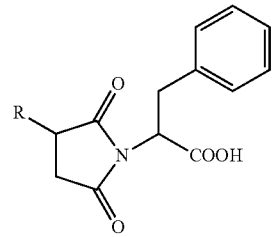

(1-2)

wherein R represents an alkyl group or an alkenyl group having a number-average molecular weight of 500 or greater and less than 5000.

5 Claims, No Drawings

(56) References Cited

FOREIGN PATENT DOCUMENTS

| EP | 1077249 | | 2/2001 |
|---|---|---|---|
| JP | 9-3463 | | 1/1997 |
| JP | 10-219269 | A | 8/1998 |
| JP | 10-265793 | | 10/1998 |
| JP | 11-199888 | | 7/1999 |
| JP | 2000-087053 | | 3/2000 |
| JP | 09823322 | | 3/2000 |
| JP | 2005-146148 | | 6/2005 |
| WO | WO 2007007054 A1 * | | 1/2007 |

OTHER PUBLICATIONS

Bradley R. et al., "Solubilisation of Acids by Succinimide-Type Ashless Dispersants," Symposium on Advances in Distillate and Residual Oil Technology, Aug. 27, 1972, pp. 101-110.

Office Action from counterpart Chinese Patent Application No. 201180017580.X, mailed on Jun. 21, 2013.

International Search Report issued with respect PCT/JP2011/057876, mailed May 31, 2011.

English-language translation of International Preliminary Report on Patentability issued with respect to PCT/JP2011/057876, mailed Nov. 22, 2012.

* cited by examiner

SUCCINIMIDE COMPOUND, LUBRICATING OIL ADDITIVE, AND LUBRICATING OIL COMPOSITION

TECHNICAL FIELD

The present invention relates to a novel succinimide compound, and a lubricating oil additive and a lubricating oil composition which contain the compound,

BACKGROUND ART

A succinimide compound is used as an ashless dispersant dispersing an insoluble to be generated, in oil in the field of a lubricating oil for an internal combustion engine such as a gasoline engine oil or a diesel engine oil. On the other hand, the succinimide compound is used as a friction modifier enhancing a friction force in the field of a driving system lubricating oil for an automatic transmission or the like.

A succinimide compound obtained by the reaction between high-molecular succinic anhydride substituted with an alkenyl or alkyl group, and polyalkylene polyamine, or the like has been known as a conventional succinimide compound (see the following Patent Literatures 1 to 3).

CITATION LIST

Patent Literature

Patent Literature 1: Japanese Patent Application Laid-Open Publication No, 2005-146148

Patent Literature 2: Japanese Patent Application Laid-Open Publication No. 10-265793

Patent Literature 3: Japanese Patent Application Laid-Open Publication No. 10-219269

SUMMARY OF INVENTION

Technical Problem

It is an object of the present invention to provide a novel succinimide compound useful for uses such as an ashless dispersant in a lubricating oil for an internal combustion engine, and a friction modifier in a driving system lubricating oil, and a lubricating oil additive and a lubricating oil composition which contain the compound.

Solution to Problem

Then, the present invention provides a succinimide compound represented by the following formula (1-1) or (1-2).

[Chemical Formula 1]

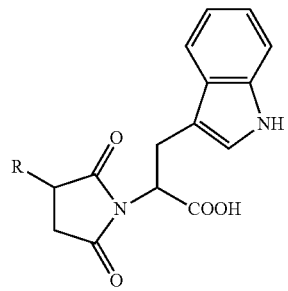

(1-1)

[In the formula (1-1), R represents an alkyl group or an alkenyl group having a number-average molecular weight of 500 or greater and less than 5000.]

[Chemical Formula 2]

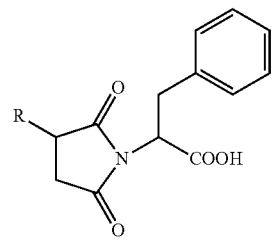

(1-2)

[In the formula (1-2), R represents an alkyl group or an alkenyl group having a number-average molecular weight of 500 or greater and less than 5000.]

Since the succinimide compound of the present invention has a very excellent characteristic as compared with a conventional succinimide compound, the succinimide compound is useful for uses such as an ashless dispersant in a lubricating oil for an internal combustion engine, and a friction modifier in a lubricating oil for a driving device.

For example, recently, a friction coefficient higher than that in the conventional manner is required for a driving system lubricating oil in order to efficiently convert a friction force in an automatic transmission into a driving force in view of improving fuel efficiency. However, when the conventional succinimide compounds described in the above Patent Literatures 1 to 3 are used, a sufficient friction characteristic-improving effect can not be obtained. This is considered to be because the friction characteristic-improving effect of the succinimide compound itself is insufficient in the case of the conventional succinimide compound, and the increased amount of succinimide changes adsorbability to a metal surface, to lose the balance of the other additive agent, thereby reducing friction characteristics.

On the other hand, since the succinimide compound of the present invention has an excellent friction characteristic-improving effect as compared with the conventional succinimide compound, the high friction coefficient for efficiently converting the friction force in the automatic transmission into the driving force can be achieved, to improve the fuel efficiency.

In the succinimide compound of the present invention, R in the formula (1-1) or (1-2) is preferably a group derived from polyisobutene having a number-average molecular weight of 500 or greater and less than 5000.

The present invention provides a lubricating oil additive containing the above succinimide compound of the present invention.

The present invention provides a lubricating oil composition containing a lubricating base oil and the above succinimide compound of the present invention.

Preferably, the lubricating oil composition of the present invention further contains a phosphorus compound.

Advantageous Effects of Invention

The present invention can provide a novel succinimide compound useful for uses such as an ashless dispersant in a lubricating oil for an internal combustion engine, and a friction modifier in a driving system lubricating oil, and a lubricating oil additive and a lubricating oil composition which contain the compound,

DESCRIPTION OF EMBODIMENTS

Hereinafter, a preferred embodiment of the present invention will be described in detail,

[Succinimide Compound]

A succinimide compound according to the embodiment has a structure represented by the following formula (1-1) or (1-2):

[Chemical Formula 3]

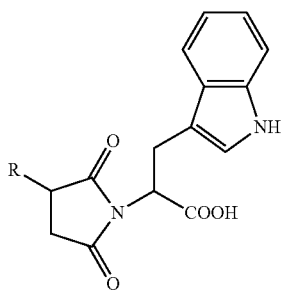

(1-1)

[In the formula (1-1), R represents an alkyl group or an alkenyl group having a number-average molecular weight of 500 or greater and less than 5000.]

[Chemical Formula 4]

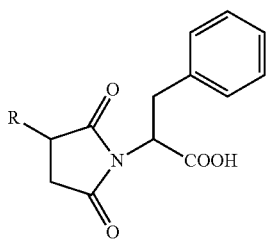

(1-2)

[In the formula (1-2), R represents an alkyl group or an alkenyl group having a number-average molecular weight of 500 or greater and less than 5000.]

A polybutenyl group and a polyisobutenyl group are preferable as the alkyl group or the alkenyl group represented by R in the formula (1-1) or (1-2). The number-average molecular weight of the alkyl group or the alkenyl group represented by R is 500 or greater and 5000 or less, preferably 700 to 4000, and more preferably 800 to 3,500.

The succinimide compound represented by the formula (1-1) can be obtained by reacting maleinized alkyl or maleinized alkenyl having the alkyl group or the alkenyl group having a number-average molecular weight of 500 or greater and less than 5000 with phenylalanine (2-amino-3-phenylpropionic acid). The above maleinized alkyl or maleinized alkenyl to be used as a raw material can be obtained by reacting polyalkene (polybutene and polyisobutene or the like) having a number-average molecular weight of 500 or greater and less than 5000 with maleic anhydride, for example.

When the maleinized alkyl or the maleinized alkenyl is reacted with the phenylalanine, the charge ratio of the maleinized alkyl or the maleinized alkenyl/the phenylalanine can be preferably set to 1/1 to 1/2 at a molar ratio, more preferably 1/1 to 1/1.8, still more preferably 1/1.1 to 1/1.6, and particularly preferably 1/1.2 to 1/1.5. The target succinimide compound can be more certainly obtained by the reaction of the above ratio of the range.

In the above reaction, a succinimide compound represented by the following formula (2-1) may be generated as a by-product in addition to the succinimide compound represented by the formula (1-1). In this case, the succinimide compound represented by the formula (2-1) is separated and removed from the reaction product, and only the succinimide compound represented by the formula (1-1) may be a lubricating oil additive. Alternatively, a mixture of the succinimide compound represented by the formula (1-1) and the succinimide compound represented by the formula (2-1) may be used as the lubricating oil additive.

[Chemical Formula 5]

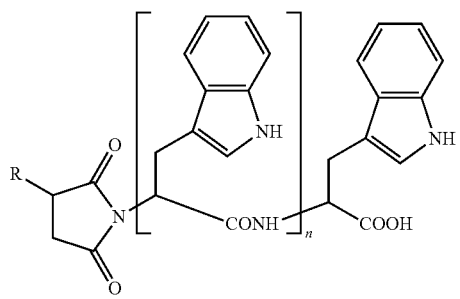

(2-1)

In the formula (2-1), R represents an alkyl group or an alkenyl group having a number-average molecular weight of 500 or greater and less than 5000. n represents an integer of 1 or greater. Although n is usually 1 or 2, n tends to be increased when the ratio of the phenylalanine to the maleinized alkyl or the maleinized alkenyl in a raw material during synthesis is increased.

The succinimide compound represented by the formula (1-2) can be obtained by reacting maleinized alkyl or maleinized alkenyl having an alkyl group or an alkenyl group having a number-average molecular weight of 500 or greater and less than 5000 with phenylalanine (2-amino-3-phenylpropionic acid). The above maleinized alkyl or maleinized alkenyl to be used as a raw material can be obtained by reacting polyalkene (polybutene and polyisobutene or the like) having a number-average molecular weight of 500 or greater and less than 5000 with maleic anhydride, for example.

When the maleinized alkyl or the maleinized alkenyl is reacted with the phenylalanine, the charge ratio of the maleinized alkyl or the maleinized alkenyl/the phenylalanine can be preferably set to 1/1 to 1/2 at a molar ratio, more preferably 1/1 to 1/1.8, still more preferably 1/1.1 to 1/1.6, and particularly preferably 1/1.2 to 1/1.5. The target succinimide compound can be more certainly obtained by the reaction of the above ratio of the range.

In the above reaction, a succinimide compound represented by the following formula (2-2) may be generated as a by-product in addition to the succinimide compound represented by the formula (1-2). In this case, the succinimide compound represented by the formula (2-2) is separated and removed from the reaction product, and only the succinimide compound represented by the formula (1-2) may be a lubricating oil additive. Alternatively, a mixture of the succinimide compound represented by the formula (1-2) and the succinimide compound represented by the formula (2-2) may be used as the lubricating oil additive,

[Chemical Formula 6]

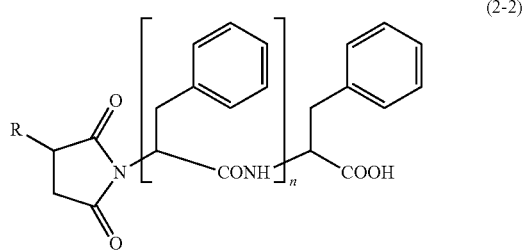

(2-2)

In the formula (2-2), R represents an alkyl group or an alkenyl group having a number-average molecular weight of 500 or greater and less than 5000, n represents an integer of 1 or greater. Although n is usually 1 or 2, n tends to be increased when the ratio of the phenylalanine to the maleinized alkyl or the maleinized alkenyl in a raw material during synthesis is increased.

The succinimide compound represented by the formula (1-1) or (1-2) may be used as it is without being borated (that is, as a non-borated succinimide compound), or may be used as a borated succinimide compound. Furthermore, the borated succinimide compound and the non-borated succinimide compound may be used in combination.

The borated succinimide compound can be obtained by reacting the succinimide compound represented by the formula (1-1) or (1-2) with a boron-containing compound at a temperature of usually 50 to 250° C., and preferably 100 to 200° C. Examples of the boron-containing compound include boron oxide, halogenized boron, boric acid, boric anhydride, and a boric acid ester. Any one of these boron-containing compounds may be used alone, or two or more thereof may be used in combination.

[Lubricating Oil Additive]

A lubricating oil additive according to the embodiment contains the succinimide compound represented by the above formula (1-1) or (1-2). The lubricating oil additive may contain only the succinimide compound represented by the formula (1-1) or (1-2), and may be a mixture of the succinimide compound represented by the formula (1-1) or (1-2) and other additive agent. The lubricating oil additive may further contain a diluent for dissolving the additive agent.

Since the succinimide compound represented by the formula (1-1) or (1-2) has excellent compatibility with various additive agents used in the field of the lubricating oil, the other additive agent used in combination is not particularly limited when the lubricating oil additive according to the embodiment is the mixture of the succinimide compound represented by the formula (1-1) or (1-2) and the other additive agent. Therefore, the kind of the other additive agent used in combination with the succinimide compound represented by the formula (1-1) or (1-2), and the mixing ratio thereof can be suitably selected according to the use and the object of the lubricating oil additive. Specific examples of the other additive agent used in combination will be described later.

A lubricating oil composition according to the embodiment contains a lubricating base oil and the succinimide compound represented by the above formula (1-1) or (1-2). A mode containing the lubricating base oil and the lubricating oil additive according to the above embodiment is included in the lubricating oil composition.

The lubricating base oil is not particularly limited, and both a mineral oil and a synthetic oil can be used. Various mineral oils which have conventionally been known can be used as the mineral oil, and examples thereof include a paraffin-based mineral oil, an intermediate-based mineral oil, and a naphthene-based mineral oil. Specific examples include a light neutral oil, an intermediate neutral oil, a heavy neutral oil, and a bright stock by solvent refining or hydrogen refining. A GTL base oil in which wax is isomerized or the like may be used, and the higher the refining degree is, the higher the effect thereof is.

Similarly, various synthetic oils which have conventionally been known can be used as the synthetic oil. For example, poly-α-olefin (including an α-olefin copolymer), polybutene, a polyol ester, a dibasic ester, a phosphoric ester, a polyphenyl ether, alkylbenzene, alkylnaphthalene, polyoxyalkylene glycol, neopentyl glycol, a silicone oil, trimethylolpropane, pentaerythritol, and a hindered ester or the like can be used.

Any one of these lubricating base oils can be used alone, or two or more thereof can be used in combination, and the mineral oil and the synthetic oil may be used in combination.

The kinetic viscosity of the lubricating base oil can be suitably selected according to the use and the object of the lubricating oil composition. When the lubricating oil composition according to the embodiment is used as a driving system lubricating oil, for example, the kinetic viscosity of the lubricating base oil at 100° C. is preferably 1 to 30 mm$^2$/s, more preferably 2 to 20 mm$^2$/s, and still more preferably 3 to 10 mm$^2$/s. When the kinetic viscosity at 100° C. is in the above range, the friction of a sliding part such as a gear bearing or a clutch of an automatic transmission can sufficiently be reduced, and the low-temperature characteristic thereof is also good. On the other hand, when the kinetic viscosity at 100° C. is greater than 30 mm$^2$/s, fuel consumption tends to be reduced, and low-temperature viscosity tends to be excessively increased. The kinetic viscosity of less than 1 mm$^2$/s at 100° C. may cause the reduction of lubricating performance such as the increase of the wear amount of the sliding part such as the gear bearing or the clutch of the automatic transmission, or cause high evaporativity to increase the amount of consumption of a lubricating oil.

The % $C_A$ of the lubricating base oil is preferably equal to or less than 20 in view of the low-temperature characteristic, and particularly more preferably equal to or less than 10.

The content of the succinimide compound represented by the formula (1-1) or (1-2) in the lubricating oil composition according to the embodiment is preferably 0.01 to 30% by mass, more preferably 0.05 to 20% by mass, and still more preferably 0.1 to 10% by mass in view of effectively exhibiting the addition effect thereof. When two or more of the succinimide compounds are used, the total of the contents thereof is preferably in the above range.

The lubricating oil composition according to the embodiment can further contain various additive agents represented by an ashless dispersant and/or a friction modifier, a metal-based cleaning agent, a viscosity index improver, an extreme-pressure agent, an antioxidant, a corrosion inhibitor, an antifoaming agent, and a colorant or the like except the succinimide compound represented by the formula (1-1) or (1-2), if needed in order to further improve the performance thereof. Any one of these additive agents can be used alone, or two or more thereof can be used in combination.

Examples of the friction modifier except the succinimide compound represented by the formula (1-1) or (1-2) include a fatty acid ester, a fatty acid amide, or a phosphorus compound such as a phosphoric ester, a phosphite, and a thiophosphoric acid ester, an organic molybdenum compound such as MoDTP or MoDTC, an organic zinc compound such as ZnDTP, an organic boron compound such as alkyl mercaptylborate, and a solid lubricant-based friction modifier such as graphite, molybdenum disulfide, an antimony sulfide, a boron compound, or polytetrafluoroethylene; of these, the phosphorus compound is preferable. The content of the friction modifier is usually 0.1 to 10% by mass based on the total amount of the lubricating oil composition.

Examples of the antioxidant include an amine-based antioxidant such as alkylated diphenylamine, phenyl-α-naphthylamine, or alkylated-α-naphthylamine, and a phenol-based antioxidant such as 2,6-di-t-butyl-4-methyl phenol or 4,4'-methylene bis(2,6-di-t-butylphenol). The content of the antioxidant is usually 0.05 to 5% by mass based on the total amount of the lubricating oil composition.

Examples of the metal-based cleaning agent include calcium sulfonate, magnesium sulfonate, barium sulfonate, calcium salicylate, magnesium salicylate, calcium phenate, and barium phenate; the content of the metal-based cleaning agent is usually 0.1 to 10% by mass based on the total amount of the lubricating oil composition.

Examples of the viscosity index improver include a polymethacrylate-based, polyisobutene-based, ethylene-propylene copolymer-based, and styrene-butadiene hydrogenated copolymer-based viscosity index improvers. The content of the viscosity index improver is usually 0.5 to 35% by mass based on the total amount of the lubricating oil composition.

The use of the lubricating oil composition according to the embodiment is not particularly limited, and the lubricating oil composition can be used in wide fields such as a lubricating oil for an internal combustion engine and a driving system lubricating oil. Since the lubricating oil composition according to the embodiment contains the succinimide compound represented by the formula (1-1) or (1-2), for example, the lubricating oil composition can achieve a high static friction coefficient as compared with a conventional succinimide compound (a high torque volume of a wet friction material), and is suitable as an automatic transmission oil and a continuously variable transmission oil. The lubricating oil composition can be used as a lubricating oil for a construction machine and a farm machine which are provided with a transmission having a wet clutch and a wet brake, a manual transmission, a two-wheeled vehicle gasoline engine, a diesel engine, a gas engine, and a shock absorber oil or the like.

EXAMPLES

Hereinafter, the present invention will be more specifically described based on Examples and Comparative Examples, and the invention is not limited to these Examples.

Example 1

Synthesis of Succinimide Compound I

After 1.0 mol of polyisobutene (number-average molecular weight: 1000) and 1.0 mol of maleic anhydride were placed in an autoclave of 2000 mL, the temperature thereof was raised to 220° C. for 1.5 hours, and the reaction was performed for 4 hours after the temperature reached 220° C. After the completion of the reaction, n-hexane was added to the obtained product, and these were stirred, and the liquid was filtered to remove an insoluble. After n-hexane was removed from the filtrate by atmospheric distillation, the maleic anhydride was removed at 220° C. under reduced pressure to obtain maleinized polyisobutene.

On the other hand, 0.008 mol of phenylalanine was crushed in a mortar, and the phenylalanine was placed in a four-necked flask of 100 mL, to which xylene was added. Next, the reaction was performed at 165° C. for 24 hours while 0.004 mol of the maleinized polyisobutene dissolved in the xylene and obtained was dropped. After the completion of the reaction, residual amino acid was removed by filtration, and a solvent was removed by distillation under reduced pressure, to obtain a succinimide compound I. The infrared absorption spectrum and elemental analysis of the obtained succinimide compound I were conducted to confirm the structure represented by the formula (1-2). The content nitrogen was 1.15 (theoretical value: 1.22) %.

Example 2

Synthesis of Succinimide Compound II

After 1.0 mol of polyisobutene (number-average molecular weight: 2300) and 1.0 mol of maleic anhydride were placed in an autoclave of 2000 mL, the temperature thereof was raised to 220° C. for 1.5 hours, and the reaction was performed for 4 hours after the temperature reached 220° C. After the completion of the reaction, n-hexane was added to the obtained product, and these were stirred, and the liquid was filtered to remove an insoluble. After n-hexane was removed from the filtrate by atmospheric distillation, the maleic anhydride was removed at 220° C. under reduced pressure to obtain maleinized polyisobutene.

On the other hand, 0.008 mol of phenylalanine was crushed in a mortar, and the phenylalanine was placed in a four-necked flask of 100 mL, to which xylene was added. Next, the reaction was performed at 165° C. for 24 hours while 0.004 mol of the maleinized polyisobutene dissolved in the xylene and obtained was dropped. After the completion of the reaction, residual amino acid was removed by filtration, and a solvent was removed by distillation under reduced pressure, to obtain a succinimide compound II. The infrared absorption spectrum and elemental analysis of the obtained succinimide compound II were conducted to confirm the structure represented by the formula (1-2). The content nitrogen was 0.54 (theoretical value: 0.57)%.

Example 3

Synthesis of Succinimide Compound III

After 1.0 mol of polyisobutene (number-average molecular weight: 1000) and 1.0 mol of maleic anhydride were placed in an autoclave of 2000 mL, the temperature thereof was raised to 220° C. for 1.5 hours, and the reaction was performed for 4 hours after the temperature reached 220° C.

After the completion of the reaction, n-hexane was added to the obtained product, and these were stirred, and the liquid was filtered to remove an insoluble. After n-hexane was removed from the filtrate by atmospheric distillation, the maleic anhydride was removed at 220° C. under reduced pressure to obtain maleinized polyisobutene.

On the other hand, 0.008 mol of phenylalanine was crushed in a mortar, and the phenylalanine was placed in a four-necked flask of 100 mL, to which xylene was added. Next, the reaction was performed at 165° C. for 24 hours while 0,004 mol of the maleinized polyisobutene dissolved in the xylene and obtained was dropped. After the completion of the reaction, residual amino acid was removed by filtration, and a solvent was removed by distillation under reduced pressure, to obtain a succinimide compound I. The infrared absorption spectrum and elemental analysis of the obtained succinimide compound I were conducted to confirm the structure represented by the formula (1-1). The content nitrogen was 1.15 (theoretical value: 1.22) %.

Example 4

Synthesis of Succinimide Compound IV

After 1.0 mol of polyisobutene (number-average molecular weight: 2300) and 1.0 mol of maleic anhydride were placed in an autoclave of 2000 mL, the temperature of the autoclave was raised to 220° C. for 1.5 hours, and the reaction was performed for 4 hours after the temperature reached 220° C. After the completion of the reaction, n-hexane was added to the obtained product, and these were stirred, and the liquid was filtered to remove an insoluble. After n-hexane was removed from the filtrate by atmospheric distillation, the maleic anhydride was removed at 220° C. under reduced pressure to obtain maleinized polyisobutene.

On the other hand, 0.008 mol of phenylalanine was crushed in a mortar, and the phenylalanine was placed in a four-necked flask of 100 mL, to which xylene was added. Next, the reaction was performed at 165° C. for 24 hours while 0.004 mol of the maleinized polyisobutene dissolved in the xylene and obtained was dropped. After the completion of the reaction, residual amino acid was removed by filtration, and a solvent was removed by distillation under reduced pressure, to obtain a succinimide compound II. The infrared absorption spectrum and elemental analysis of the obtained succinimide compound II were conducted to confirm the structure represented by the formula (1-1). The content nitrogen was 0.54 (theoretical value: 0.57) %.

Comparative Example 1

Synthesis of Succinimide Compound V

After 1.0 mol of polyisobutene (number-average molecular weight: 1000) and 1.0 mol of maleic anhydride were placed in an autoclave of 2000 mL, the temperature thereof was raised to 220° C. for 1.5 hours, and the reaction was performed for 4 hours after the temperature reached 220° C. After the completion of the reaction, n-hexane was added to the obtained product, and these were stirred, and the liquid was filtered to remove sludge. After n-hexane was removed from the filtrate by atmospheric distillation, the maleic anhydride was removed at 220° C. under reduced pressure to obtain maleinized polyisobutene.

1.7 mol of diethylene triamine and xylene were placed in a separable flask of 2 L. Next, the reaction was performed at 145 to 155° C. for 11 hours while 0.17 mol of the maleinized polybutene dissolved in the xylene and obtained was dropped. After the completion of the reaction, a solvent was removed by atmospheric distillation, and residual diethylene triamine was removed by distillation under reduced pressure, to obtain a succinimide compound V.

Examples 5 to 16 and Comparative Examples 2 to 4

Preparation and Evaluation Test of Lubricating Oil Composition

In Examples 5 to 16 and Comparative Examples 2 to 4, lubricating oil compositions were prepared using a mineral oil of an SAE10 distillate (kinetic viscosity at 100° C.: 4.1 mm$^2$/s) as a lubricating base oil, a succinimide compound I, II, III, IV or V, and additive agents shown in Tables 1 and 2. The compositions of the lubricating oil compositions are shown in Tables 1 to 3.

Next, intermetallic friction coefficients of the lubricating oil compositions of Examples 5 to 16 and Comparative Examples 2 to 4 were evaluated using an LFW-1 test machine. The test conditions: surface pressure, slide rate, test temperature, and test time were set to 0.8 GPa, 0.2 m/s, 80° C., and 1 hour, respectively, and the intermetallic friction coefficients were evaluated using an average friction coefficient obtained by averaging the friction coefficients within the time. The obtained results are shown in Tables 1 to 3.

TABLE 1

|  |  | Example 5 | Example 6 | Example 7 | Example 8 | Example 9 | Example 10 |
|---|---|---|---|---|---|---|---|
| Composition (% by mass) | Base oil SAE10 | Balance | Balance | Balance | Balance | Balance | Balance |
|  | Polymethacrylate | 4 | 4 | 4 | 4 | 4 | 4 |
|  | Amine-based antioxidant | 0.25 | 0.25 | 0.25 | 0.25 | 0.25 | 0.25 |
|  | Tricresyl phosphate | 0.9 | 0.9 | 0.9 | 0.9 | 0.9 | 0.9 |
|  | Calcium sulfonate | 0.3 | 0.3 | 0.3 | 0.3 | 0.3 | 0.3 |
|  | Ashless-based oily agent | 0.1 | 0.1 | 0.1 | 0.1 | 0.1 | 0.1 |
|  | Succinimide I (PIB: 1000) | 0.5 | 2.0 | 4.0 | — | — | — |
|  | Succinimide II (PIB: 2300) | — | — | — | 0.5 | 2.0 | 4.0 |
| Intermetallic friction coefficient (LFW-1 average friction coefficient) |  | 0.130 | 0.150 | 0.159 | 0.126 | 0.144 | 0.148 |

TABLE 2

|  |  | Example 11 | Example 12 | Example 13 | Example 14 | Example 15 | Example 16 |
|---|---|---|---|---|---|---|---|
| Composition (% by mass) | Base oil SAE10 | Balance | Balance | Balance | Balance | Balance | Balance |
|  | Polymethacrylate | 4 | 4 | 4 | 4 | 4 | 4 |
|  | Amine-based antioxidant | 0.25 | 0.25 | 0.25 | 0.25 | 0.25 | 0.25 |
|  | Tricresyl phosphate | 0.9 | 0.9 | 0.9 | 0.9 | 0.9 | 0.9 |
|  | Calcium sulfonate | 0.3 | 0.3 | 0.3 | 0.3 | 0.3 | 0.3 |
|  | Ashless-based oily agent | 0.1 | 0.1 | 0.1 | 0.1 | 0.1 | 0.1 |
|  | Succinimide III (PIB: 1000) | 0.5 | 2.0 | 4.0 | — | — | — |
|  | Succinimide IV (PIB: 2300) | — | — | — | 0.5 | 2.0 | 4.0 |
| Intermetallic friction coefficient (LFW-1 average friction coefficient) |  | 0.128 | 0.144 | 0.156 | 0.122 | 0.140 | 0.143 |

TABLE 3

|  |  | Comparative Example 2 | Comparative Example 3 | Comparative Example 4 |
|---|---|---|---|---|
| Composition (% by mass) | Base oil SAE10 | Balance | Balance | Balance |
|  | Polymethacrylate | 4 | 4 | 4 |
|  | Amine-based antioxidant | 0.25 | 0.25 | 0.25 |
|  | Tricresyl phosphate | 0.9 | 0.9 | 0.9 |
|  | Calcium sulfonate | 0.3 | 0.3 | 0.3 |
|  | Ashless-based oily agent | 0.1 | 0.1 | 0.1 |
|  | Succinimide V | 1.4 | 2.8 | — |
| Intermetallic friction coefficient (LFW-1 average friction coefficient) |  | 0.122 | 0.126 | 0.103 |

INDUSTRIAL APPLICABILITY

The succinimide compound, the lubricating oil additive, and the lubricating oil composition of the present invention can be used in the wide field of the lubricating oils, and are particularly suitable as an automatic transmission oil and a continuously variable transmission oil which require a high static friction coefficient.

The invention claimed is:

1. A succinimide compound represented by the following formula (1-1) or (1-2):

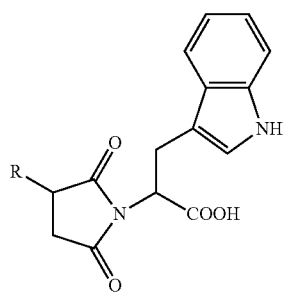

(1-1)

wherein R represents an alkyl group or an alkenyl group having a number-average molecular weight of 500 or greater and less than 5000;

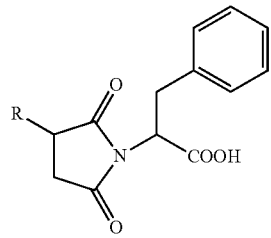

(1-2)

wherein R represents an alkyl group or an alkenyl group having a number-average molecular weight of 500 or greater and less than 5000.

2. The succinimide compound according to claim 1, wherein R in the formula (1-1) or (1-2) is a group derived from polyisobutene having a number-average molecular weight of 500 or greater and less than 5000.

3. A lubricating oil additive comprising the succinimide compound according to claim 1.

4. A lubricating oil composition comprising a lubricating base oil and the succinimide compound according to claim 1.

5. The lubricating oil composition according to claim 4, further comprising a phosphorus compound.

* * * * *